US012667120B2

(12) United States Patent　　(10) Patent No.:　US 12,667,120 B2
Badri et al.　　(45) Date of Patent:　Jun. 30, 2026

(54) PET FOOD COMPOSITIONS

(71) Applicant: Hill's Pet Nutrition, Inc., Topeka, KS (US)

(72) Inventors: Dayakar Badri, Lawrence, KS (US); Dennis Jewell, Lawrence, KS (US)

(73) Assignee: Hill's Pet Nutrition, Inc., Overland Park, KS (US)

( * ) Notice: Subject to any disclaimer, the term of this patent is extended or adjusted under 35 U.S.C. 154(b) by 571 days.

(21) Appl. No.: 18/248,816

(22) PCT Filed: Oct. 12, 2021

(86) PCT No.: PCT/US2021/054496
§ 371 (c)(1),
(2) Date: Apr. 12, 2023

(87) PCT Pub. No.: WO2022/081524
PCT Pub. Date: Apr. 21, 2022

(65) Prior Publication Data
US 2023/0397637 A1　　Dec. 14, 2023

Related U.S. Application Data

(60) Provisional application No. 63/091,513, filed on Oct. 14, 2020.

(51) Int. Cl.
| | |
|---|---|
| *A23K 20/158* | (2016.01) |
| *A23K 10/30* | (2016.01) |
| *A23K 20/147* | (2016.01) |
| *A23K 50/42* | (2016.01) |
| *A61K 31/202* | (2006.01) |
| *A61K 36/55* | (2006.01) |
| *A61K 36/899* | (2006.01) |
| *A61P 3/04* | (2006.01) |

(52) U.S. Cl.
CPC ............ *A23K 20/158* (2016.05); *A23K 10/30* (2016.05); *A23K 20/147* (2016.05); *A23K 50/42* (2016.05); *A61K 31/202* (2013.01); *A61K 36/55* (2013.01); *A61K 36/899* (2013.01); *A61P 3/04* (2018.01)

(58) Field of Classification Search
CPC .... A23K 20/158; A23K 10/30; A23K 20/147; A23K 50/42; A61K 31/202; A61K 36/55; A61K 36/899; A61P 3/04
See application file for complete search history.

(56) References Cited

U.S. PATENT DOCUMENTS

| | | | |
|---|---|---|---|
| 6,071,544 | A | 6/2000 | Sunvold |
| 6,716,815 | B2 | 4/2004 | Portman |
| 8,529,965 | B2 | 9/2013 | Yamka et al. |
| 9,168,240 | B2 | 10/2015 | Yamka et al. |

| | | | |
|---|---|---|---|
| 2003/0068357 | A1 | 4/2003 | Vala et al. |
| 2009/0148560 | A1 | 6/2009 | Shiba et al. |
| 2015/0242566 | A1 | 8/2015 | Samer |

FOREIGN PATENT DOCUMENTS

| | | |
|---|---|---|
| JP | 2010-518851 A | 6/2010 |
| JP | 2013-135690 A | 7/2013 |
| JP | 2016-202077 A | 12/2016 |
| WO | 2008/103179 A1 | 8/2008 |
| WO | 2012/087512 A1 | 6/2012 |

OTHER PUBLICATIONS

Chen et al., 2018, "Exploring the Link between Serum Levels and Low Muscle Strength, Dynapenia, and Sarcopenia," Scientific Reports 8:3573.
Diez et al., 2002, "Weight Loss in Obese Dogs: Evaluation of a High-Protein, Low-Carbohydrate Diet," J. Nutr. 132: 1685S-1687S.
Ellingsen et al., 2015, "Impact of red cell distribution width on future risk of cancer and all-cause mortality among cancer patients—the Tromsø Study," haematologica 100:e387-e389.
German, A., 2006, "The Growing Problem of Obesity in Dogs and Cats," J Nutrition 136: 1940S-1946S.
German, A., 2010, "A high protein high fibre diet improves weight loss in obese dogs," The Veterinary Journal 183 294-297.
Goyal et al., 2014, "Flax and flaxseed oil: an ancient medicine & modern functional food", Journal of Food Science and Technology, vol. 51(9): 1633-1653.
International Search Report and the Written Opinion of the International Searching Authority issued in International Application PCT/US2021/054496 mailed Jan. 21, 2022.
Karakas et al., 2016, "Red cell distribution width and neutrophil-to-lymphocyte ratio predict left ventricular dysfunction In acute anterior ST-segment elevation myocardial infarction," J Saudi Heart Assoc 28:152-158.
Kendrick et al., 2011, "Phosphate and Cardiovascular Disease," Adv Chronic Kidney Dis. 18(2): 113-119.
Li et al., 2017, "Effects of the Dietary Protein and Carbohydrate Ratio on Gut Microbiomes in Dogs of Different Body Conditions," mBio 8(1): e01703-16.
Lippi et al., 2009, "Relation between red blood cell distribution width and inflammatory biomarkers in a large cohort of unselected outpatients," Arch Pathol Lab Med 133:628-632.
Phillips et al., 2017, "Feline Obesity in Veterinary Medicine: Insights from a Thematic Analysis of Communication in Practice," Frontiers Veterinary Science 4:117.
Piantedosi et al., 2016, "Serum biochemistry profile, inflammatory cytokines, adipokines and cardiovascular findings in obese dogs," The Veterinary Journal 216 (2016) 72-78.
Rein et al., 2019, ""I don't get no respect": the role of chloride in acute kidney injury," Am J Physiol Renal Physiol 316: F587-F605.
Tarkosova et al., 2016, "Feline obesity—prevalence, risk factors, athogenesis, associated conditions and assessment: a review,"Veterinarni Medicina, 61, 2016 (6): 295-307.

(Continued)

*Primary Examiner* — Trevor Love

(57) ABSTRACT

Described herein are pet food compositions and methods for using them. Such compositions may comprise soluble fiber and certain ratios of linolenic acid to fatty acids. The methods may include feeding the pet an effective amount of the pet food composition. The methods may include increasing the lean mass of a companion animal comprising feeding an effective amount of a pet food composition comprising soluble fiber and certain ratios of linolenic acid to fatty acids.

17 Claims, No Drawings

(56)            References Cited

OTHER PUBLICATIONS

Tonelli et al., 2008, "Relation Between Red Blood Cell Distribution Width and Cardiovascular Event Rate in People With Coronary Disease," Circulation 117:163-168.

Van Baak et al., 2017, "Dietary Intake of Protein from Different Sources and Weight Regain, Changes in Body Composition and Cardiometabolic Risk Factors after Weight Loss: The DIOGenes Study," Nutrients 9:1326.

Wang et al., 2016, "Association between chloride-rich versus chloride-restrictive intravenous fluid administration and acute kidney injury in cardiovascular patients in ICU wards," Exp Therapeutic Medicine 12:987-990.

Wen, Y., 2015, "High red blood cell distribution width is closely associated with risk of carotid artery atherosclerosis in patients with hypertension," Exp Clin Cardiol 15(3):37-40.

Yamka et al., 2007, "Effects of 3 Canine Weight Loss Foods on Body Composition and Obesity Markers", Intern J Appl Res Vet Med, vol. 5, No. 3, pp. 125-132.

Official Publication of the Associate of American Feed Control Officials, Inc. ("AAFCO"), Nutrient Requirements of Dogs and Cats, 2006.

PET FOOD COMPOSITIONS

CROSS-REFERENCE TO RELATED APPLICATION APPLICATIONS

This application is a U.S. National Stage application of PCT/US2021/054496, filed Oct. 12, 2021, which claims the benefit of priority from U.S. Provisional Application No. 63/091,513, filed Oct. 14, 2020, the contents of which are hereby incorporated herein by reference in their entireties.

BACKGROUND

Obesity is a serious health threat to pets. According to the 2019 survey of Association of Pet Obesity Prevention (APOP) the obesity rates of cats and dogs in the US was 59.5% and 55.8% respectively. Other diseases such as diabetes mellitus, osteoarthritis, cardiovascular, skin disorders and decreased lifespan are considered as comorbid conditions with obesity (Phillips et al. 2017; German AJ. 2006, 2016; Tarkosova et al. 2016).

The well-being of domestic animals is closely related to their feeding. Correct feeding should result in a fit and healthy pet. To achieve correct feeding, one may utilize certain ingredients and concentrations of those ingredients which yield beneficial effects for the animal. Such beneficial effects may include reducing fat mass, increasing lean mass, or improving clinical parameters such as reducing blood triglycerides and red blood cell distribution width (RDW).

It would therefore be desirable to provide a pet food composition which may beneficially affect obese animals, such as by increasing the lean mass of the animal.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Applicants have discovered that utilization of certain ingredients within a pet food composition provides for effective health benefits. In one aspect, the health benefit may be to increase the lean mass of the animal. In another aspect, the health benefit may be to increase the lean mass of an obese animal. In another aspect, the health benefit may be to increase the lean mass of a dog. Thus, in one aspect, the invention is a pet food composition comprising soluble fiber and certain mass ratios of linolenic acid to fatty acids.

In at least one embodiment, the present invention is directed to a pet food composition comprising soluble fiber present in an amount of about 0.5% or more, based on the dry weight of the pet food composition; and a mass ratio of linolenic acid to total 18 carbon polyunsaturated fatty acids ((linolenic acid):(total 18 carbon polyunsaturated fatty acids)) of about 0.39 or greater. In some embodiments, the ratio of linolenic acid to total 18 carbon polyunsaturated fatty acids is from about 0.3 to about 1. In some embodiments, the ratio of linolenic acid to total 18 carbon polyunsaturated fatty acids is from 0.3 to about 0.8. In some embodiments, the ratio of linolenic acid to total 18 carbon polyunsaturated fatty acids is from about 0.3 to about 0.5. In some embodiments, the ratio of linolenic acid to total 18 carbon polyunsaturated fatty acids is about 0.39. In some embodiments, the soluble fiber is present in an amount of about 3% to about 12%, based on the dry weight of the pet food composition. In some embodiments, the soluble fiber is present in an amount of about 3% to about 10%, based on the dry weight of the pet food composition. In some embodiments, the soluble fiber is present in an amount of about 3.5% to about 7%, based on the dry weight of the pet food composition. In some embodiments, the total dietary fiber is present in an amount of less than 20%, based on the dry weight of the pet food composition. In some embodiments, the total dietary fiber is present in an amount of about 10% to about 20%, based on the dry weight of the pet food composition. In some embodiments, the total dietary fiber is present in an amount of about 10% to about 18%, based on the dry weight of the pet food composition. In some embodiments, the total dietary fiber is present in an amount of about 15% to about 18%, based on the dry weight of the pet food composition. In some embodiments, moisture is present in an amount of about 5% to about 15%, based on the weight of the pet food composition. In some embodiments, moisture is present in an amount of about 8% to about 13%, based on the weight of the pet food composition. In some embodiments, moisture is present in an amount of about 9% to about 11%, based on the weight of the pet food composition. In some embodiments, the composition comprises protein present in an amount of about 25% to about 40%, based on the dry weight of the pet food composition. In some embodiments, the composition comprises protein present in an amount of about 30% to about 40%, based on the dry weight of the pet food composition. In some embodiments, the composition further comprises protein present in an amount of about 30% to about 35%, based on the dry weight of the pet food composition. In some embodiments, the composition comprises flax seed in an amount of about 7% and rye berries in an amount of about 4.4%, based on the dry weight of the pet food composition. In some embodiments, the composition is a kibble.

In further embodiments, the invention is directed to a method for treating, preventing, or ameliorating a symptom of obesity in a companion animal, comprising feeding an effective amount of the composition according to any one of the embodiments described above to a companion animal in need thereof. In certain embodiments, the companion animal is a dog.

In other embodiments, the invention is directed to a method for increasing the lean mass of a companion animal comprising feeding an effective amount of a pet food composition comprising soluble fiber present in an amount of about 0.5% or more, based on the dry weight of the pet food composition; and a ratio of linolenic acid to total 18 carbon polyunsaturated fatty acids of about 0.39 or greater. In some embodiments, the ratio of linolenic acid to total 18 carbon polyunsaturated fatty acids is from about 0.3 to about 1. In some embodiments, the ratio of linolenic acid to total 18 carbon polyunsaturated fatty acids is from 0.3 to about 0.8. In some embodiments, the ratio of linolenic acid to total 18 carbon polyunsaturated fatty acids is from about 0.3 to about 0.5. In some embodiments, the ratio of linolenic acid to total 18 carbon polyunsaturated fatty acids is about 0.39. In some embodiments, the soluble fiber is present in an amount of about 3% to about 12%, based on the dry weight of the pet food composition. In some embodiments, the soluble fiber is present in an amount of about 3% to about 10%, based on the dry weight of the pet food composition. In some embodiments, the soluble fiber is present in an amount of about 3.5% to about 7%, based on the dry weight of the pet food composition. In some embodiments, the total dietary fiber is present in an amount of less than 20%, based on the dry weight of the pet food composition. In some embodiments, the total dietary fiber is present in an amount of about 10% to about 20%, based on the dry weight of the pet food composition. In some embodiments, the total dietary fiber is present in an amount of about 10% to about 18%, based on the dry weight of the pet food composition. In some embodiments, the total dietary fiber is present in an amount of about 15% to about 18%, based on the dry weight of the pet food composition. In some embodiments, moisture is present in an amount of about 5% to about 15%, based on the weight of the pet food composition. In some embodiments, moisture is present in an amount of about 8% to about 13%, based on the weight of the pet food composition. In some embodiments, moisture is present in an amount of about 9% to about 11%, based on the weight of the pet food composition. In some embodiments, the composition comprises protein present in an amount of about 25% to about 40%, based on the dry weight of the pet food composition. In some embodiments, the composition comprises protein present in an amount of about 30% to about 40%, based on the dry weight of the pet food composition. In some embodiments, the composition comprises protein present in an amount of about 30% to about 35%, based on the dry weight of the pet food composition. In some embodiments, the composition comprises flax seed in an amount of about 7% and rye berries in an amount of about 4.4%, based on the dry weight of the pet food composition. In some embodiments, the pet food composition is a kibble. In some embodiments, the companion animal is a dog.

Further areas of applicability of the present invention will become apparent from the detailed description provided hereinafter. It should be understood that the detailed description and specific examples, while indicating the typical embodiments of the invention, are intended for purposes of illustration only and are not intended to limit the scope of the invention.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other applications and methods. It is to be understood that the invention is not limited in its application to the details of any particular embodiment shown. The terminology used herein is for the purpose of description and not to limit the invention, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", "containing", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight of the total composition. Reference to a molecule, or to molecules, being present at a "wt. %" refers to the amount of that molecule, or molecules, present in the composition based on the total weight of the composition.

According to the present application, use of the term "about" in conjunction with a numeral value refers to a value that may be +/−5% of that numeral. As used herein, the term "substantially free" is intended to mean an amount less than about 5.0 weight %, less than 3.0 weight %, 1.0 wt. %; preferably less than about 0.5 wt. %, and more preferably less than about 0.25 wt. % of the composition.

Unless defined otherwise, all technical and scientific terms used herein have the same meanings as commonly understood by one of ordinary skill in the art to which this invention belongs. All patents, patent applications, publications, and other references cited or referred to herein are incorporated by reference in their entireties for all purposes. In the event of a conflict in a definition in the present disclosure and that of a cited reference, the present disclosure controls.

The present disclosure is directed toward pet food compositions and methods of using such pet food compositions for the treatment of domestic pets. In certain embodiments, the pet is a dog. In other embodiments, the dog is obese.

The present inventors have surprisingly and unexpectedly discovered that providing animals a pet food diet comprising soluble fiber and a high ratio of linolenic acid to total 18 carbon polyunsaturated fatty acids provides for enhanced health benefit for the animal. Such enhanced health benefit may be exemplified by numerous aspects. In a first aspect, the health benefit may be to increase the lean mass of the animal. In another aspect, the health benefit may be to increase the lean mass of an obese animal. In another aspect, the health benefit may be to increase the lean mass of an obese dog.

In one aspect, the present disclosure therefore provides pet food compositions comprising soluble fiber present in an amount of about 0.5% or more, based on the dry weight of the pet food composition; and a ratio of linolenic acid to total 18 carbon polyunsaturated fatty acids of about 0.39 or greater. In certain embodiments, the pet food is in a dry form. In certain embodiments, the pet food is a kibble.

The soluble fiber may be present at various amounts or concentrations. In one embodiment, soluble fiber may be present in an amount of about 0.5 weight % or more, such as from about 0.5 to about 20 weight %, based on the dry weight of the pet food composition. For example, the soluble fiber may be present in an amount of about 2.0 weight %, about 2.5 weight %, about 3.0 weight %, about 3.5 weight %, about 4.0 weight %, about 4.5 weight %, about 5 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, about 10.0 weight %, about 10.5 weight %, about 11.0 weight %, about 12.0 weight %, about 12.5 weight %, about 13.0 weight %, about 13.5 weight %, about 14.0 weight %, about 14.5 weight %, about 15.0 weight %, about 15.5 weight %, about 16.0 weight %, about 16.5 weight %, about 17.0 weight %, about 18.0 weight %, or about 20.0 weight %, including all ranges and subranges therebetween, based on the dry weight of the pet food composition. For example, the pet food composition may comprise soluble fiber in an amount of about 0.5 to about 20 weight %, about 0.5 to about 15 weight %, about 0.5 to about 10 weight %, about 0.5 to about 8 weight %, about 0.5 to about 6 weight %, about 0.5 to about 5 weight %, about 0.5 to about 4 weight %, about 0.5 to about 3 weight %; about 1 to about 20 weight %, about 1 to about 15 weight %, about 1 to about 10 weight %, about 1 to about 8 weight %, about 1 to about 6 weight %, about 1 to about 5 weight %, about 1 to about 4 weight %, about 1 to about 3 weight %; about 1.5 to about 20 weight %, about 1.5 to about 15 weight %, about 1.5 to about 10 weight %, about 1.5 to about 8 weight %, about 1.5 to about 6 weight %, about 1.5 to about 5 weight %, about 1.5 to about 4 weight %, about 1.5 to about 3 weight %; about 2 to about 20 weight %, about 2 to about 15 weight %, about 2 to about 10 weight %, about 2 to about 8 weight %, about 2 to about 6 weight %, about 2 to about 5 weight %, about 2 to about 4 weight %, about 2 to about 3 weight %; about 2.5 to about 20 weight %, about 2.5 to about 15 weight %, about 2.5 to about 10 weight %, about 2.5 to about 8 weight %, about 2.5 to about 6 weight %, about 2.5 to about 5 weight %, about 2.5 to about 4 weight %; about 3 to about 20 weight %, about 3 to about 15 weight %, about 3 to about 10 weight %, about 3 to about 8 weight %, about 3 to about 6 weight %, about 3 to about 5 weight %, or about 3 to about 4 weight %, including all ranges and subranges thereof, based on the dry weight of the pet food composition.

In another example, the soluble fiber may be present in an amount of from about 3% to about 12%, about 3% to about 10%, or about 3.5% to about 7%, based on the dry weight of the pet food composition. In further embodiments, the soluble fiber is present in an amount of about 3% or more, about 3.5% or more, about 3.7% or more, or about 4.0% or more, based on the dry weight of the pet food composition. In further embodiments, the soluble fiber is present in an amount of about 3% to 4%, about 3% to about 5%, about 3% to about 10%, or about 3% to about 20%, based on the dry weight of the pet food composition.

The pet food compositions includes one or more fatty acid(s) in an amount typically from about 0.5 to about 20 weight %, based on the total weight of the pet food composition. For example, the pet food composition may comprise one or more fatty acid(s) in an amount of about 0.5 to about 20 weight %, about 0.5 to about 15 weight %, about 0.5 to about 10 weight %, about 0.5 to about 8 weight %, about 0.5 to about 6 weight %, about 0.5 to about 5 weight %, about 0.5 to about 4 weight %, about 0.5 to about 3 weight %; about 1 to about 20 weight %, about 1 to about 15 weight %, about 1 to about 10 weight %, about 1 to about 8 weight %, about 1 to about 6 weight %, about 1 to about 5 weight %, about 1 to about 4 weight %, about 1 to about 3 weight %; about 1.5 to about 20 weight %, about 1.5 to about 15 weight %, about 1.5 to about 10 weight %, about 1.5 to about 8 weight %, about 1.5 to about 6 weight %, about 1.5 to about 5 weight %, about 1.5 to about 4 weight %, about 1.5 to about 3 weight %; about 2 to about 20 weight %, about 2 to about 15 weight %, about 2 to about 10 weight %, about 2 to about 8 weight %, about 2 to about 6 weight %, about 2 to about 5 weight %, about 2 to about 4 weight %, about 2 to about 3 weight %; about 2.5 to about 20 weight %, about 2.5 to about 15 weight %, about 2.5 to about 10 weight %, about 2.5 to about 8 weight %, about 2.5 to about 5 weight %, about 2.5 to about 6 weight %, about 2.5 to about 5 weight %, about 2.5 to about 4 weight %; about 3 to about 20 weight %, about 3 to about 15 weight %, about 3 to about 10 weight %, about 3 to about 8 weight %, about 3 to about 6 weight %, about 3 to about 5 weight %, or about 3 to about 4 weight %, including all ranges and subranges thereof, based on the dry weight of the pet food composition.

The one or more fatty acid(s) are preferably chosen from those having 10 to 50 total carbon atoms, from 10 to 40 total carbon atoms, or from 10 to 30 total carbon atoms. In some embodiments, the pet food compositions have a total number of carbon atoms of 10 to 30, 12 to 28, 14 to 26, 16 to 24, 16 to 22, or 16 to 20. Preferably, the pet food composition comprises one or more fatty acids chosen from polyunsaturated fatty acids. In one preferred embodiment, the pet food composition comprises a polyunsaturated fatty acid having a total of 18 carbon atoms.

The fatty acid may be derived from a plant source. Without being limited to any particular theory, it is believed fatty acids obtained or derived from a plant source may provide enhanced benefits as compared to fatty acids derived from animal sources. Examples of plant sources for deriving or obtaining the fatty acids include, e.g., flaxseed, algae, avocado, hemp seeds, pumpkin seeds, sunflower seeds, walnuts, soya, or combinations of two or more thereof. In some embodiments, however, the fatty acids are derived from an animal source or synthesized.

The fatty acids may be comprised of omega-3, linolenic acid, omega-6, stearic acid, arachidic acid, oleic acid, stearidonic acid, eicosapentaenoic acid, linolelaidic acid cervonic acid, docosatetraenoic acid, palmitoleic acid, vaccenic acid, paullinic acid, elaidic acid, gondoic acid, erucic acid, nervonic acid, mead acid, or a combination of two or more thereof. In some instances, the fatty acid comprises omega-3, omega-6, vaccenic acid, oleic acid, elaidic acid, linolelaidic acid, linoleic acid, stearidonic acid, or a combination of two or more thereof. Preferably, the pet food compositions comprise linoleic acid, such as α-linolenic acid and/or γ-linolenic acid.

The pet food compositions may, for some embodiments, be formulated to have a weight ratio of linolenic acid to total polyunsaturated fatty acids of from about 0.3 to about 2. For instance, the weight ratio of linolenic acid to total polyunsaturated fatty acids is from about 0.3 to about 1.8, about 0.3 to about 1.5, about 0.3 to about 1.25, about 0.3 to about 1, about 0.3 to about 0.8, about 0.3 to about 0.6, about 0.3 to about 0.5, about 0.3 to about 0.5; about 0.35 to about 1.8, about 0.35 to about 1.5, about 0.35 to about 1.25, about 0.35 to about 1, about 0.35 to about 0.8, about 0.35 to about 0.6, about 0.35 to about 0.5, about 0.35 to about 0.5; about 0.38 to about 1.8, about 0.38 to about 1.5, about 0.38 to about 1.25, about 0.38 to about 1, about 0.38 to about 0.8, about 0.38 to about 0.6, about 0.38 to about 0.5, about 0.38 to about 0.5; about 0.4 to about 1.8, about 0.4 to about 1.5, about 0. to about 1.25, about 0.4 to about 1, about 0.4 to about 0.8, about 0.4 to about 0.6, about 0.4 to about 0.5, about 0.4 to about 0.5. In some embodiments, the weight ratio of linolenic acid to total polyunsaturated fatty acids is about 0.39.

Additionally or alternatively, the pet food composition comprises linolenic acid and total 18 carbon polyunsaturated fatty acids at certain mass ratios. In certain embodiments, the mass ratio of linolenic acid to total 18 carbon polyunsaturated fatty acids is from about 0.3 to about 2. In other embodiments, the mass ratio of linolenic acid to total 18 carbon polyunsaturated fatty acids is from about 0.3 to about 1. In certain embodiments, the ratio of linolenic acid to total 18 carbon polyunsaturated fatty acids is from about 0.3 to about 0.8, about 0.3 to about 0.6, about 0.3 to about 0.5, or about 0.3 to about 0.5. In further embodiments, the ratio of linolenic acid to total 18 carbon polyunsaturated fatty acids is about 0.39. In other embodiments, the mass ratio of linolenic acid to total 18 carbon polyunsaturated fatty acids is from about 0.3 to about 1.8, or about 0.39. In some embodiments, the weight ratio of linolenic acid to total 18 carbon polyunsaturated fatty acids is from about 0.3 to about 1.8, about 0.3 to about 1.5, about 0.3 to about 1.25, about 0.3 to about 1, about 0.3 to about 0.8, about 0.3 to about 0.6, about 0.3 to about 0.5, about 0.3 to about 0.5; about 0.35 to about 1.8, about 0.35 to about 1.5, about 0.35 to about 1.25, about 0.3 to about 1, about 0.35 to about 0.8, about 0.35 to about 0.6, about 0.35 to about 0.5, about 0.35 to about 0.5; about 0.38 to about 1.8, about 0.38 to about 1.5, about 0.38 to about 1.25, about 0.38 to about 1, about 0.38 to about 0.8, about 0.38 to about 0.6, about 0.38 to about 0.5, about 0.38 to about 0.5; about 0.4 to about 1.8, about 0.4 to about 1.5, about 0. to about 1.25, about 0.4 to about 1, about 0.4 to about 0.8, about 0.4 to about 0.6, about 0.4 to about 0.5, about 0.4 to about 0.5.

The pet food compositions may have a beneficial weight ratio of soluble fiber to fatty acids. Specifically, it is believed that the weight ratio of soluble fiber to fatty acids may promote weight loss, leanness, and/or lean muscle mass in certain weight ratios. For example, the pet food composition may have a weight ratio of soluble fiber to fatty acids of from about 10:1 to about 1:10, about 7:1 to about 1:10, about 5:1 to about 1:10, about 3:1 to about 1:10, about 2:1 to about 1:10; about 10:1 to about 1:7, about 7:1 to about 1:7, about 5:1 to about 1:7, about 3:1 to about 1:7, about 2:1 to about 1:7; about 10:1 to about 1:5, about 7:1 to about 1:5, about 5:1 to about 1:5, about 3:1 to about 1:5, about 2:1 to about 1:5 about 10:1 to about 1:3, about 7:1 to about 1:3, about 5:1 to about 1:3, about 3:1 to about 1:3, about 2:1 to about 1:3; about 10:1 to about 1:2, about 7:1 to about 1:2, about 5:1 to about 1:2, about 3:1 to about 1:2, or about 2:1 to about 1:2.

The moisture of the composition may be present at various amounts or concentrations. The moisture may be present at various amounts or concentrations. In one embodiment, the moisture may be present in an amount of from about 5% to about 15%, based on the weight of the pet food composition. For example, the moisture may be present in an amount of about 5.0 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, about 10.0 weight %, about 10.5 weight %, about 11.0 weight %, about 11.5 weight %, about 12.0 weight %, about 12.5 weight %, about 13.0 weight %, about 13.5 weight %, about 14.0 weight %, about 14.5 weight %, or about 15.0 weight %. In another example, the moisture may be present in an amount of from about 8% to about 13%, about 9% to about 13%, about 9% to about 11%, or about 9% to about 13%, based on the weight of the pet food composition. In certain embodiments, the moisture is present in an amount of about 10% to about 12%, about 10.5% to about 12%, or about 10.5% to about 11.5%, based on the weight of the pet food composition.

The protein of the composition may be present at various amounts or concentrations. In one embodiment, the protein may be present in an amount of from about 20% to about 45%, based on the dry weight of the pet food composition. For example, the protein may be present in an amount of about 20 weight %, about 25 weight %, about 30 weight %, about 35 weight %, about 40 weight %, or about 45 weight. In another example, the protein may be present in an amount of from about 25% to about 40%, from about 30% to about 40%, or about 30% to about 35%, based on the dry weight of the pet food composition. In certain embodiments, the protein is present in an amount of about 20% to about 35%, about 25% to about 35%, or about 28% to about 35%, based on the dry weight of the pet food composition.

The pet food composition may comprise protein and/or a digestible crude protein. "Digestible crude protein" is the portion of protein that is available or can be converted into free nitrogen (amino acids) after digesting with gastric enzymes. In vitro measurement of digestible crude protein may be accomplished by using gastric enzymes such as pepsin and digesting a sample and measuring the free amino acid after digestion. In vivo measurement of digestible crude protein may be accomplished by measuring the protein levels in a feed/food sample and feeding the sample to an animal and measuring the amount of nitrogen collected in the animal's feces.

A portion of the protein in the composition may be digestible protein. For example, the composition may include an amount of protein, where about 40 weight % or more, about 50 weight % or more, about 60 weight % or more, about 70 weight % or more, about 80 weight % or more, or about 90 weight % or more of the protein is digestible protein. In some embodiments, e.g., when the composition desirable promotes weight loss, the portion of protein that is digestible protein is about 60 weight % or less, about 50 weight % or less, about 40 weight % or less, about 30 weight % or less, about 20 weight % or less, or about 10 weight % or less, based on the total amount of protein in the composition. In further embodiment, the amount of protein that is digestible protein is about 10 to about 90 weight %, about 10 to about 70 weight %, about 10 to about 50 weight %, about 10 to about 30 weight %; about 30 to about 90 weight %, about 30 to about 70 weight %, about 30 to about 50 weight %; about 50 to about 90 weight %, about 50 to about 70 weight %; or about 70 to about 90 weight %, including ranges and subranges therein, based on the total amount of protein in the composition.

The compositions of the present invention may optionally comprise additional ingredients suitable for use in pet food compositions. Examples of such ingredients include, but are not limited to, fat, carbohydrates, dietary fibers, amino acids, minerals, trace elements, vitamins, additives.

Dietary fiber refers to components of a plant which are resistant to digestion by an animal's digestive enzymes. Dietary fiber includes soluble and insoluble fibers. Soluble fibers are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, fructooligosaccharides (FOS), or peas. Insoluble fibers can be supplied by any of a variety of sources, including, for example, cellulose, whole wheat products, wheat oat, corn bran, flax seed, grapes, celery, green beans, cauliflower, potato skins, fruit skins, vegetable skins, peanut hulls, rye berries, sweet potato, and soy fiber. Crude fiber includes indigestible components contained in cell walls and cell contents of plants such as grains, for example, hulls of grains such as rice, corn, and beans. Typical crude fiber amounts in compositions of the present disclosure can be from about 0 to 10%, or about 1% to about 5%.

The total dietary fiber may be present at various amounts or concentrations. In one embodiment, total dietary fiber may be present in an amount of less than 20%, based on the dry weight of the pet food composition. In certain embodiments, the total dietary fiber is present in an amount of about 10% to about 20%, based on the dry weight of the pet food composition. For example, total dietary fiber may be present in an amount of about 10.0 weight %, about 10.5 weight %, about 11.0 weight %, about 11.5 weight %, about 12.0 weight %, about 12.5 weight %, about 13.0 weight %, about 13.5 weight %, about 14.0 weight %, about 14.5 weight %, about 15.0 weight %, about 15.5 weight %, about 16.0 weight %, about 16.5 weight %, about 17.0 weight %, about 17.5 weight %, about 18.0 weight %, about 18.5 weight %, about 19.0 weight %, about 19.5 weight %, or about 20.0 weight %. In another example, total dietary fiber may be present in an amount of from about 10% to about 18%, about 12% to about 18%, or about 15% to about 18%, based on the dry weight of the pet food composition. In further embodiments, total dietary fiber is present in an amount of about 15% to about 20%, about 16% to about 19%, or about 16% to about 18%, based on the dry weight of the pet food composition.

Amino acids, including essential amino acids, can be added to the compositions of the present disclosure as free amino acids, or supplied by any number of sources, e.g., crude protein, to the compositions of the present disclosure. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine. In addition, taurine, while technically not an amino acid but a derivative of cysteine, is an essential nutrient for cats.

The compositions of the present invention may optionally comprise fat. The term "fat" generally refers to a lipid or mixture of lipids that may generally be a solid or a liquid at ordinary room temperatures (e.g., 25° C.) and pressures (e.g., 1 atm). In some instances, the fat may be a viscous liquid or an amorphous solid at standard room temperature and pressure. Fat can be supplied by any of a variety of sources known by those skilled in the art, including meat, meat by-products, canola oil, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The compositions of the present disclosure may contain at least about 9% (or from about 9% to about 25%, or from about 10% to about 20%, or from about 10% to about 15%) total fat.

In some cases, the fat in the compositions is crude fat. Crude fat may be included into the compositions in amounts of from about 10 to about 20 weight %, about 10 to about 18 weight %, about 10 to about 16 weight %; about 12 to about 20 weight %, about 12 to about 18 weight %, about 12 to about 16 weight %, about 12 to about 14 weight %, or about 12 to about 13 weight %, based on the total weight of the composition. In some cases, it may be preferable that about 50 weight % or more, about 60 weight % or more, about 70 weight % or more, about 80 weight % or more, or about 90 weight % or more of the total fat is obtained from an animal source. Alternatively, about 50 weight % or more, about 60 weight % or more, about 70 weight % or more, about 80 weight % or more, or about 90 weight % or more of the total fat may be obtained from a plant source.

Carbohydrates can be supplied by any of a variety of sources known by those skilled in the art, including oat fiber, cellulose, peanut hulls, beet pulp, parboiled rice, corn starch, corn gluten meal, and any combination of those sources. Grains supplying carbohydrates can include, but are not limited to, wheat, corn, barley, and rice. Carbohydrates content of foods can be determined by any number of methods known by those of skill in the art. Generally, carbohydrate percentage can be calculated as nitrogen free extract ("NFE"), which can be calculated as follows: NFE=100%-moisture %-protein %-fat %-ash %-crude fiber %. The amount of carbohydrate, e.g., calculated as NFE, present in the composition may be about 10 to about 90 weight %, about 10 to about 70 weight %, about 10 to about 50 weight %, about 10 to about 40 weight %, about 10 to about 30 weight %, about 10 to about 20 wt. %; about 20 to about 90 weight %, about 20 to about 70 weight %, about 20 to about 50 weight %, about 20 to about 40 weight %; about 30 to about 90 weight %, about 30 to about 70 weight %, about 30 to about 50 weight %, about 30 to about 40 weight %; about 50 to about 90 weight %, about 50 to about 70 weight %; or about 70 to about 90 weight %, based on the total weight of the composition.

The compositions of the present disclosure can also contain one or more minerals and/or trace elements, e.g., calcium, phosphorus, sodium, potassium, magnesium, manganese, copper, zinc, chromium, molybdenum, selenium, or iron salts having counterions such as, for example chloride, iodide, fluoride, sulfide or oxide, in amounts required to avoid deficiency and maintain health. These amounts are known by those of skill in the art, for example, as provided in the Official Publication of the Associate of American Feed Control Officials, Inc. ("AAFCO"), Nutrient Requirements of Dogs and Cats, 2006. Typical mineral amounts are about 0.1% to about 4% or about 1% to about 2%.

The compositions of the present invention can also include vitamins in amounts required to avoid deficiency and maintain health. These amounts and methods of measurement are known by those skilled in the art. For example, the Official Publication of the Associate of American Feed Control Officials, Inc. ("AAFCO"), Nutrient Requirements of Dogs and Cats, 2006 provides recommended amounts of such ingredients for dogs and cats. As contemplated herein, vitamins can include, but are not limited to, vitamin A, vitamin B.sub.1, vitamin B.sub.2, vitamin B.sub.6, vitamin B.sub.12, vitamin C, vitamin D, vitamin E, vitamin H (biotin), vitamin K, folic acid, choline, inositol, niacin, and pantothenic acid. Typical vitamin amounts in the composition of the invention are about from 0 to about 3% or about 1% to about 2%.

The compositions of the present disclosure can additionally comprise other additives such as palatability enhancers and stabilizers in amounts and combinations familiar to one of skill in the art. Stabilizing substances include, for example, substances that tend to increase the shelf life of the composition. Other examples of other such additives potentially suitable for inclusion in the compositions of the invention include, for example, preservatives, colorants, antioxidants, flavorants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches. The concentration of such additives in the composition typically can be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Foods of any consistency or moisture content are contemplated, e.g., the compositions of the present invention can be, for example, a dry, moist or semi-moist animal food composition. In some embodiments, the moisture content is from about 3% to about 90% of the total weight of the composition. "Semi-moist" refers to a food composition containing from about 25 to about 35% moisture. "Moist" food refers to a food composition that has a moisture content of about 60 to 90% or greater. "Dry" food refers to a food composition with about 3 to about 12% moisture content and is often manufactured in the form of small bits or kibbles.

In certain aspects, the present application further discloses a method of making any of the compositions of the present disclosure. In preparing a composition of the present invention in wet or canned form, any ingredient (e.g., soluble fiber and desired ratio of linolenic acid):(total 18 carbon polyunsaturated fatty acids) generally can, for example, be incorporated into the composition during the processing of the formulation, such as during and/or after mixing of other components of the composition. Distribution of these components into the composition can be accomplished by conventional means. In some embodiments, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients can be mixed in a vessel suitable for heating while blending the components. Heating of the mixture can be effected using any suitable manner, such as, for example, by direct steam injection or by using a vessel fitted with a heat exchanger. Following the addition of the last ingredient, the mixture can be heated to a temperature range of from about 50° F. (10° C.) to about 212° F. (100° C.). In some instances, the mixture can be heated to a temperature range of from about 70° F. (21° C.) to about 140° F. (60° C.). Temperatures outside these ranges are generally acceptable but may be commercially impractical without use of other processing aids. When heated to the appropriate temperature, the material will typically be in the form of a thick liquid. The thick liquid can be filled into cans. When filled into cans, a lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Pet food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, then forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

In another aspect, the present disclosure provides a method for increasing the lean mass of a companion animal, comprising feeding the animal a pet food composition as described herein in an amount effective to increase the lean mass of the animal. The companion animal may be a dog or cat. In a preferred embodiment, such increase in the beneficial metabolite biomarkers is more than would occur under conditions where one or more of the specified ingredients are not present, or are not present at desired ratios. In some embodiments, the method for increasing the lean mass of a companion animal comprises feeding an effective amount of a pet food composition comprising soluble fiber present in an amount of about 3.5% or more, based on the dry weight of the pet food composition and having a ratio of linolenic acid to total 18 carbon polyunsaturated fatty acids of about 0.39 or greater.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Twenty-one obese beagles and one obese mixed breed dog were used in the study design. The dogs were 1.11 to 12.6 years old, weighing 9.1 to 17.4 kg, and spayed or neutered. Feeding was performed following a cross-over design where all dogs were fed a control food in a pre-feed phase for four weeks and then were divided into two groups for phase one studies. During phase one, Group 1 was fed Composition 1 for 8 weeks and Group 2 was fed Composition 2 for 8 weeks. Afterwards, both groups were fed the control food for four weeks as a washout period. Next, phase two studies were performed which included feeding Group 1 Composition 2 and feeding Group 2 Composition 1 for 8 weeks. All three food compositions were fed based on the particular dog's caloric requirement, which was calculated based on that dog's current body weight. Dual-energy X-ray absorptiometry (DEXA) analysis was performed at the end of pre-feed, phase one, and phase two. Blood/serum and fecal samples were collected at the end of pre-feed, phase one, washout, and phase two. A control group was evaluated based on dogs receiving the control food under similar testing conditions.

Food compositions were formulated as described in Table 1. All compositions were fed as kibble, generated by extrusion, dried and coated with palatants. Numerical values represent the weight percent of that component, based on the dry weight of the pet food composition.

TABLE 1

| Dog Food Compositions (wt. %) | | | |
| --- | --- | --- | --- |
| Ingredient | Control | Composition 1 | Composition 2 |
| Beet Pulp | 5.3 | 11 | 9.25 |
| Cellulose | 10.348 | 1.152 | 1.152 |
| Chicken fat acidified | 4.8 | 1 | 1 |
| Chicken meal | 5.98 | 16.5 | 15 |
| Corn, gluten, meal | 19.95 | 8.99 | 10 |
| Corn, yellow, whole | 23.904 | 12.5 | 7.75 |
| Flax seed | 0.25 | 7 | 7.25 |
| Pea fiber | 8.1 | 0 | 0 |
| Dicalcium phosphate | 0.05 | 0 | 0 |

TABLE 1-continued

| Dog Food Compositions (wt. %) | | | |
|---|---|---|---|
| Ingredient | Control | Composition 1 | Composition 2 |
| Oat fiber | 0 | 0 | 1.602 |
| Oat groats | 0 | 0 | 4.4 |
| Rye berries | 0 | 0 | 4.4 |
| Sweet potato granules | 0 | 17.001 | 13.848 |
| Fructooligosaccharides (FOS), short chain | 0 | 0.5 | 0 |
| Other common ingredients | 21.318 | 21.357 | 21.348 |

TABLE 2

| Macronutrient Concentrations of Dog Food Compositions (wt. %) | | | |
|---|---|---|---|
| Analyte | Control | Composition 1 | Composition 2 |
| Ash | 5.17 | 8.23 | 7.63 |
| Fat crude | 10.75 | 12.19 | 12.3 |
| Fiber crude | 12.2 | 4.8 | 4.8 |
| Insoluble fiber | 20.6 | 13.8 | 13.2 |
| Soluble fiber | 2.7 | 3.8 | 3.5 |
| Fiber, total dietary | 23.3 | 17.6 | 16.7 |
| Moisture | 11.29 | 10.7 | 11.41 |
| Protein crude | 29.94 | 31.38 | 30.94 |
| CHO | 30.65 | 32.7 | 32.92 |
| (Linolenic acid): (total 18 carbon polyunsaturated fatty acids) | 0.0661 | 0.3925 | 0.3945 |

Example 2

Results of the feeding studies from Example 1 are shown in Table 3. Numerical values outside parenthesis represent the mean while numerical values within parenthesis represent the standard deviation.

TABLE 3

| Result Summary | | | |
|---|---|---|---|
| Analyte | Control | Composition 1 | Composition 2 |
| Mean Intake (Kcal/metabolic body weight) | 104.68 (10.84) | 112.43 (12.65) | 115.05 (14.12) |
| (Soluble Fiber Intake)/ (metabolic body weight) | 0.89 (0.092) | 1.27 (0.143) | 1.19 (0.146) |
| Lean body mass (g) | 7058.5 (1311.3) | 7228.3 (1330) | 7273 (1268.8) |

Animals fed a diet comprising a ratio of linolenic acid to total 18 carbon polyunsaturated fatty acids of at least 0.39 (Composition 1 and Composition 2) surprisingly a) exhibited higher amounts of lean body mass, and b) exhibited higher soluble fiber intake when compared to animals fed a diet comprising a lower ratio of linolenic acid to total 18 carbon polyunsaturated fatty acids ratio of 0.0661. Without being bound by theory, it is believed that any change in lean body mass is a direct result of the food composition.

TABLE 4

| Result Summary | | | |
|---|---|---|---|
| Analyte | Control vs. Composition 1 | Control vs. Composition 2 | Composition 1 vs. Composition 2 |
| Triglycerides (mg/dL) | −0.0004 | −0.0003 | 0.9965 |
| RDW (fl) | −0.0066 | 0.0002 | 0.5871 |

Table 4 shows p value results from analysis on DEXA, blood CBC, chemscreen and fecal variables. Results were derived using mixed model followed by Tukey post-hoc significance analysis. A negative number represents a decrease compared to control.

Example 3

Further compositions were prepared to evaluate the health benefits for pet food compositions comprising lower levels of soluble fiber and a ratio of linolenic acid to total 18 carbon polyunsaturated fatty acids of less than 0.39. Table 5 summarizes the compositions.

TABLE 5

| Result Summary | | | |
|---|---|---|---|
| Analyte | Composition 3 | Composition 4 | Composition 5 |
| Soluble Fiber | 1.44 | 1.15 | 1.45 |
| (Linolenic acid):(total 18 carbon polyunsaturated fatty acids) | 0.263 | 0.201 | 0.197 |

Example 4

Results of the feeding study from Example 3 are shown in Table 6.

TABLE 6

| Analyte Quantification | | | |
|---|---|---|---|
| Analyte | Composition 3 | Composition 4 | Composition 5 |
| Change in lean mass (g) | −470 | −370 | −411 |

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

Example 5

Microbiome sequencing was performed on the fecal matter of the dogs to further evaluate the effect of food compositions 1 and 2. Specifically, fecal samples from the dogs were collected within 30 minutes after defecation, homogenized, aliquoted in 2 ml cryovials, snap frozen with liquid nitrogen, and then stored in 70° C. for further processing.

The fecal samples were analyzed for microbiome sequencing by extracting total DNA from the frozen samples using a MoBio PowerFecal DNA extraction kit, which was commercially available from QIAGEN, with modifications. Subsequently, 16s rDNA amplicon was developed from the total DNA samples using a PCR and primer sets spanning the V3 and V4 hypervariable regions. The amplicons were then analyzed qualitatively using a 2100 Bioanalyzer, produced by AGILENT.

Index PCR was performed, followed by library quantification, normalization and pooling of the samples by following manufacturer's instructions with modifications. The final pooled sample library was loaded in a MiSeq v3 sample loading cartridge kit and the cartridge was placed in a MiSeq sequencer—the cartridge kit and sequencer device were available from ILLUMINA—for sequencing the amplicons. The sample sequences were demultiplexed using MiSeq's in-built "metagenomics" workflow to obtain FASTQ files. FASTQ files were processed by employing MOTHUR software to classify the sequence reads using Greengenes database followed by custom modifications.

For the microbiome analyses, the abundance data at the phyla, family, and genera levels, were filtered based upon by prevalence (>50%) in the data set and the percentage of reads retained per sample (>99.0%). After dataset filtering, the count data was transformed into centered log-ratio (CLR) values to enable appropriate statistical analysis using ALDEx2 R package. Diversity measures were evaluated as Shannon index, richness and evenness was calculated by using unfiltered data at the genera level. As a crossover design study, mixed model analysis was performed by using food type as fixed effect and animal identification as a random effect with false discovery rate (FDR)-corrected P values. The resultant reduced model P values were FDR-adjusted with the Benjamini-Hochberg correction. Tukey's post hoc test was used to assess pairwise differences across diet types for each analyte.

Based on the fecal microbiome analyses, Compositions 1 and 2 showed significant increase of the phyla Bacteroidetes and Fusobacteria than the control food. Additionally, the Bacteroidets to Firmicutes (B:F) ratio was greater for Compositions 1 and 2 as compared with control food (see Table 7). On the contrary, Compositions 1 and 2 significantly decreased the abundance of phyla Firmicutes compared with control food.

TABLE 7

| Microbiome | Overall model Food effect_FDR adjusted P value | Control | Composition 1 | Composition 2 |
|---|---|---|---|---|
| *Phyla* | | | | |
| *Bacteroidetes* | 0.0054 | $0.29 \pm 0.38^b$ | $1.43 \pm 0.26^a$ | $1.39 \pm 0.31^a$ |
| *Firmicutes* | <0.0001 | $5.17 \pm 0.27^a$ | $4.19 \pm 0.15^b$ | $4.09 \pm 0.16^b$ |
| *Fusobacteria* | <0.0001 | $-0.42 \pm 0.22^b$ | $0.87 \pm 0.14^a$ | $0.53 \pm 0.1^a$ |
| B:F ratio | 0.0063 | $0.13 \pm 0.08^b$ | $0.38 \pm 0.07^a$ | $0.39 \pm 0.08^a$ |

There was a consistency in the increase of phylum Bacteroidetes, and particularly family Bacteroidaceae (see Table 8) and the genus *Bacteroides* (see Table 9) for dogs receiving Compositions 1 and 2 as compared with those receiving the control food. The interaction of *Bacteroides* and a host dog is considered to correct the immune system mediated by capsular polysaccharide components from *Bacteroides* species. Further, it is believed that increasing the B:F ratio may promote or support weight loss in animals, such as dogs.

TABLE 8

| | Overall model Food effect_ FDR adjusted P value | Control | Composition 1 | Composition 2 |
|---|---|---|---|---|
| *Family* | | | | |
| *Bacteroidaceae* | <0.0001 | $1.63 \pm 0.33^b$ | $4.12 \pm 0.32^a$ | $4 \pm 0.3^a$ |
| *Clostridiaceae* | 0.0001 | $7.33 \pm 0.29^a$ | $6.19 \pm 0.31^b$ | $6.18 \pm 0.34^b$ |
| *Fusobacteriaceae* | <0.0001 | $4.25 \pm 0.27^b$ | $5.66 \pm 0.21^a$ | $5.44 \pm 0.17^a$ |
| *Peptococcaceae* | 0.0371 | $1.51 \pm 0.34^a$ | $0.24 \pm 0.45^{ab}$ | $-0.2 \pm 0.61^b$ |
| *Prevotellaceae* | 0.0386 | $3.79 \pm 0.57^b$ | $5.19 \pm 0.3^a$ | $5.25 \pm 0.31^a$ |
| *Ruminococcaceae* | <0.0001 | $4.87 \pm 0.19^b$ | $6.48 \pm 0.31^a$ | $6.09 \pm 0.28^a$ |
| *Turicibacteraceae* | <0.0001 | $7.1 \pm 0.38^a$ | $4.81 \pm 0.44^b$ | $4.41 \pm 0.46^b$ |
| *Veillonellaceae* | 0.0007 | $3.6 \pm 0.34^b$ | $5.37 \pm 0.17^a$ | $5.1 \pm 0.34^a$ |

TABLE 9

| | Overall model Food_ effect FDR adjusted P value | Control | Composition 1 | Composition 2 |
|---|---|---|---|---|
| *Genera* | | | | |
| *Bacteroides* | <0.0001 | $2.44 \pm 0.33^b$ | $4.74 \pm 0.31^a$ | $4.54 \pm 0.31^a$ |
| *Blautia* | <0.0001 | $7.6 \pm 0.3^a$ | $6.42 \pm 0.24^b$ | $6.47 \pm 0.28^b$ |
| *Clostridium* | 0.0002 | $7.17 \pm 0.27^a$ | $6.29 \pm 0.28^b$ | $6.1 \pm 0.28^b$ |
| *Dorea* | 0.0095 | $5.36 \pm 0.31^a$ | $4.48 \pm 0.35^b$ | $4.4 \pm 0.35^b$ |
| *Faecalibacterium* | <0.0001 | $5.46 \pm 0.23^b$ | $7.01 \pm 0.3^a$ | $6.51 \pm 0.26^a$ |
| *Fusobacterium* | 0.0001 | $2.25 \pm 0.31^b$ | $3.8 \pm 0.28^a$ | $3.55 \pm 0.26^a$ |
| *Lachnospira* | <0.0001 | $-3.07 \pm 0.6^b$ | $1.12 \pm 1.02^a$ | $2.85 \pm 0.74^a$ |
| *Megamonas* | <0.0001 | $1.71 \pm 0.32^b$ | $3.89 \pm 0.35^a$ | $3 \pm 0.45^a$ |
| *Peptococcus* | 0.0158 | $2.37 \pm 0.35^a$ | $0.91 \pm 0.47^{ab}$ | $0.34 \pm 0.63^b$ |
| *Turicibacter* | <0.0001 | $7.97 \pm 0.38^a$ | $5.49 \pm 0.42^b$ | $5 \pm 0.44^b$ |

Similarly, Phylum Fusobacteria, family Fusobacteriaceae and genus *Fusobacterium* was significantly increased by Compositions 1 and 2 as compared with the control food (see Table 7, 8, and 9). Phylum Fusobacteria is abundant in dogs and is generally believed to be associated with the leanness of dogs. A greater abundance of Fusobacteria is generally considered to be harmful in humans due to its association with colon cancer. On the contrary, Fusobacteria has an indispensable role in the health maintenance of dogs. For instance, Fusobacteria is generally believed to decrease gastrointestinal diseases in dogs. In addition, microbial diversity and evenness was significantly improved in the dogs receiving Compositions 1 or 2 as compared to the dogs receiving the control food (see Table 10).

TABLE 10

| | Overall model Food effect_ FDR adjusted P value | Control | Composition 1 | Composition 2 |
|---|---|---|---|---|
| Diversity measures | | | | |
| Shannon index | <0.0001 | 2.64 ± 0.06[b] | 2.94 ± 0.03[a] | 2.96 ± 0.04[a] |
| Evenness | <0.0001 | 0.61 ± 0.01[b] | 0.67 ± 0.007[a] | 0.68 ± 0.009[a] |
| Richness | 0.0852 | 72.8 ± 1.93[a] | 77.05 ± 1.55[a] | 77.47 ± 1.74[a] |

Example 6

Fecal short-chain fatty acids (SCFAs) were analyzed by METABOLON INC. As a crossover design study, mixed model analysis was performed by using food type as fixed effect and animal identification as a random effect with false discovery rate (FDR)-corrected P values. The resultant reduced model P values were FDR-adjusted with the Benjamini-Hochberg correction. Tukey's post hoc test was used to assess pairwise differences across diet types for each analyte.

Branched chain fatty acids are generally produced by bacteria using branched amino acids as substrates and are indicators of detrimental putrefaction. Fecal branched chain fatty acids (isovaleric and 2-methylbutyric) levels were significantly reduced by Compositions 1 and 2 compared to the control food (see Table 11). In addition, the dogs receiving Compositions 1 and 2 had a significant increase of straight chain fatty acids (acetate, propionate, butyrate) as compared with dogs receiving the control food. Fecal short chain fatty acids data suggests that Compositions 1 and 2 reduced detrimental branched chain fatty acids and increased beneficial straight chain fatty acids production.

TABLE 11

| | Overall model Food effect_ FDR adjusted P value | Control | Composition 1 | Composition 2 |
|---|---|---|---|---|
| Diversity measures | | | | |
| Shannon index | <0.0001 | 2.64 ± 0.06[b] | 2.94 ± 0.03[a] | 2.96 ± 0.04[a] |
| Evenness | <0.0001 | 0.61 ± 0.01[b] | 0.67 ± 0.007[a] | 0.68 ± 0.009[a] |
| Richness | 0.0852 | 72.81 ± 1.93[a] | 77.05 ± 1.55[a] | 77.47 ± 1.74[a] |

Overall, Composition 1 and 2 significantly improved the gut microbiome by increasing beneficial bacterial abundance, diversity, evenness, B:F ratio, and increasing postbiotics, such as straight chain fatty acids. Additionally, Compositions 1 and 2 decreased branched chain fatty acids for the improvement of overall gut health during a weight loss period.

What is claimed is:

1. A pet food composition comprising:
soluble fiber present in an amount of about 3 to 10 weight %; and
one or more fatty acids, the one or more fatty acids comprising linolenic acid, wherein the total dietary fiber is present in an amount of less than 20 weight % and the pet food composition has a weight ratio of linolenic acid to total 18 carbon polyunsaturated fatty acids of about 0.39 to about 1; and
wherein all weight percentages are based on a total weight of the pet food composition.

2. The pet food composition according to claim 1, wherein the one or more fatty acids are from a plant source, and wherein the one or more fatty acids are from flaxseed, algae, avocado, hemp seeds, pumpkin seeds, sunflower seeds, walnuts, soya, or a combination thereof.

3. The pet food composition according to claim 1, wherein the one or more fatty acids are selected from fatty acids having 10 to 50 total carbon atoms.

4. The pet food composition according to claim 1, wherein the one or more fatty acids further comprises at least one fatty acid selected from omega-3, omega-6, stearic acid, arachidic acid, oleic acid, stearidonic acid, eicosapentaenoic acid, linolelaidic acid, cervonic acid, docosatetraenoic acid, palmitoleic acid, vaccenic acid, paullinic acid, elaidic acid, gondoic acid, erucic acid, nervonic acid, mead acid, or a combination thereof.

5. The pet food composition according to claim 1, wherein the one or more fatty acids further comprises at least one fatty acid selected from omega-3, omega-6, vaccenic acid, oleic acid, elaidic acid, linolelaidic acid, linoleic acid, stearidonic acid, or a combination thereof.

6. The pet food composition according to claim 1, wherein the pet food composition has a weight ratio of linolenic acid to fatty acids of about 0.39 to about 1.

7. The pet food composition according to claim 1, wherein the soluble fiber is present in an amount of about 3.5 to about 7 weight %.

8. The pet food composition according to claim 1, wherein the pet food composition has a weight ratio of soluble fiber to fatty acids of from about 10:1 to about 1:10.

9. A pet food composition comprising:
soluble fiber present in an amount of about 3 to 10 weight % or more; and
a weight ratio of linolenic acid to total 18 carbon polyunsaturated fatty acids of about 0.39 to about 1,
wherein the total dietary fiber is present in an amount of less than 20 weight %, and
wherein all weight percentages are based on a total weight of the pet food composition.

10. The pet food composition according to claim 9, wherein the ratio of linolenic acid to total 18 carbon polyunsaturated fatty acids is from 0.39 to about 0.8.

11. The pet food composition according to claim 9, wherein the ratio of linolenic acid to total 18 carbon polyunsaturated fatty acids is from about 0.39 to about 0.5.

12. The pet food composition according to claim 9, wherein moisture is present in an amount of about 5 to about 15 weight %.

13. The pet food composition according to claim 9, wherein the composition further comprises protein present in an amount of about 25 to about 40 weight %.

14. The pet food composition according to claim 9, wherein the composition comprises flax seed in an amount of about 7 weight % and rye berries in an amount of about 4.4 weight %.

15. A method for treating, preventing, or ameliorating a symptom of obesity in a companion animal, comprising feeding an effective amount of the pet food composition of claim 1 to the companion animal in need thereof.

16. The method of claim 15, wherein the companion animal is a dog.

17. A method for increasing the lean mass of a companion animal, the method comprising feeding the companion animal in need thereof an effective amount of the pet food composition of claim 9.

\* \* \* \* \*